US011135093B2

United States Patent
Loerner et al.

(10) Patent No.: US 11,135,093 B2
(45) Date of Patent: Oct. 5, 2021

(54) PATIENT INTERFACE FOR OPHTHALMIC SURGERY

(71) Applicant: Alcon Inc., Fribourg (CH)

(72) Inventors: Johannes Loerner, Rosstal (DE); Peter Riedel, Nuremberg (DE)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 16/210,677

(22) Filed: Dec. 5, 2018

(65) Prior Publication Data

US 2019/0175400 A1   Jun. 13, 2019

Related U.S. Application Data

(60) Provisional application No. 62/597,779, filed on Dec. 12, 2017.

(51) Int. Cl.
*A61F 9/009* (2006.01)
*A61F 9/008* (2006.01)
*A61B 3/10* (2006.01)

(52) U.S. Cl.
CPC .......... *A61F 9/009* (2013.01); *A61F 9/00825* (2013.01); *A61B 3/102* (2013.01); *A61F 2009/00872* (2013.01)

(58) Field of Classification Search
None
See application file for complete search history.

(56) References Cited

U.S. PATENT DOCUMENTS

| | | | | |
|---|---|---|---|---|
| 4,558,698 A | * | 12/1985 | O'Dell | A61F 9/00781 351/219 |
| 4,573,778 A | * | 3/1986 | Shapiro | A61B 3/10 351/159.33 |
| 4,665,913 A | * | 5/1987 | L'Esperance, Jr. | A61F 9/009 606/3 |
| 4,732,148 A | * | 3/1988 | L'Esperance, Jr. | A61F 9/00804 606/5 |
| 4,796,623 A | * | 1/1989 | Krasner | A61F 9/013 600/565 |
| 4,905,711 A | * | 3/1990 | Bennett | A61F 9/007 128/869 |

(Continued)

FOREIGN PATENT DOCUMENTS

EP   3167853 A1   5/2017

OTHER PUBLICATIONS

"Streamline your surgery center"; website: https://www.myalcon.com/products/surgical/lensx-laser/softfit.shtml.

*Primary Examiner* — Carl H Layno
*Assistant Examiner* — Manolis Pahakis

(57) ABSTRACT

In certain embodiments, a patient interface apparatus for ophthalmic surgery comprises an annular member and an evacuation conduit. The annular member has an outer side, an inner side, a distal side, and a proximal side. The inner side defines an opening that allows for a laser beam to reach a treatment region of an eye free from reflection or refraction. The proximal side has a contact surface shaped to affix to a surface of the eye, and a groove that defines a suction chamber with the surface of the eye. The evacuation conduit is capable of fluid communication with the suction chamber, and conducts fluid away from the suction chamber to affix the contact surface to the surface of the eye.

11 Claims, 3 Drawing Sheets

(56) References Cited

U.S. PATENT DOCUMENTS

| | | | | |
|---|---|---|---|---|
| 4,923,467 A * | 5/1990 | Thompson | A61B 17/00491 | 128/898 |
| 5,108,388 A * | 4/1992 | Trokel | A61F 9/008 | 606/13 |
| 5,108,412 A * | 4/1992 | Krumeich | A61F 9/009 | 604/294 |
| 5,141,506 A * | 8/1992 | York | A61F 9/00804 | 128/898 |
| 5,505,723 A * | 4/1996 | Muller | A61F 9/008 | 606/10 |
| 5,772,675 A * | 6/1998 | Hellenkamp | A61F 9/009 | 606/166 |
| 5,779,696 A * | 7/1998 | Berry | A61F 9/0079 | 606/10 |
| 5,807,380 A * | 9/1998 | Dishler | A61F 9/00802 | 606/166 |
| 6,059,805 A * | 5/2000 | Sugimura | A61F 9/013 | 606/166 |
| 6,344,040 B1 * | 2/2002 | Juhasz | A61F 9/00827 | 606/4 |
| 6,436,113 B1 * | 8/2002 | Burba | A61F 9/008 | 606/166 |
| 6,520,956 B1 * | 2/2003 | Huang | A61F 9/008 | 606/10 |
| 6,730,074 B2 * | 5/2004 | Bille | A61F 9/00825 | 128/898 |
| 7,611,507 B2 * | 11/2009 | Raksi | A61F 9/009 | 606/4 |
| 8,858,581 B2 | 10/2014 | Robl et al. | | |
| 2002/0103481 A1 * | 8/2002 | Webb | A61F 9/009 | 606/5 |
| 2005/0107773 A1 * | 5/2005 | Bergt | A61F 9/0084 | 606/4 |
| 2006/0247660 A1 * | 11/2006 | Perez | A61F 9/007 | 606/107 |
| 2006/0287662 A1 * | 12/2006 | Berry | A61F 9/009 | 606/166 |
| 2007/0016292 A1 * | 1/2007 | Perez | A61F 9/0133 | 351/159.02 |
| 2007/0219542 A1 * | 9/2007 | Yahagi | A61F 9/008 | 606/5 |
| 2007/0237620 A1 * | 10/2007 | Muhlhoff | A61F 9/009 | 414/751.1 |
| 2007/0255355 A1 * | 11/2007 | Altshuler | A61B 18/203 | 607/86 |
| 2008/0071254 A1 | 3/2008 | Lummis et al. | | |
| 2008/0208177 A1 * | 8/2008 | Mrochen | A61F 9/008 | 606/5 |
| 2009/0024117 A1 * | 1/2009 | Muller | A61B 18/14 | 606/20 |
| 2010/0274228 A1 * | 10/2010 | Mrochen | A61F 9/013 | 604/541 |
| 2011/0112519 A1 * | 5/2011 | Donitzky | A61F 9/00836 | 606/4 |
| 2012/0078241 A1 * | 3/2012 | Gooding | A61F 9/009 | 606/6 |
| 2013/0041354 A1 | 2/2013 | Brownell | | |
| 2013/0053837 A1 * | 2/2013 | Kandulla | A61F 9/009 | 606/4 |
| 2013/0231644 A1 | 9/2013 | Hanft et al. | | |
| 2016/0095752 A1 | 4/2016 | Srinivasan | | |
| 2017/0128261 A1 * | 5/2017 | Deisinger | A61F 9/00825 | |
| 2017/0239087 A1 | 8/2017 | Sahler et al. | | |

* cited by examiner

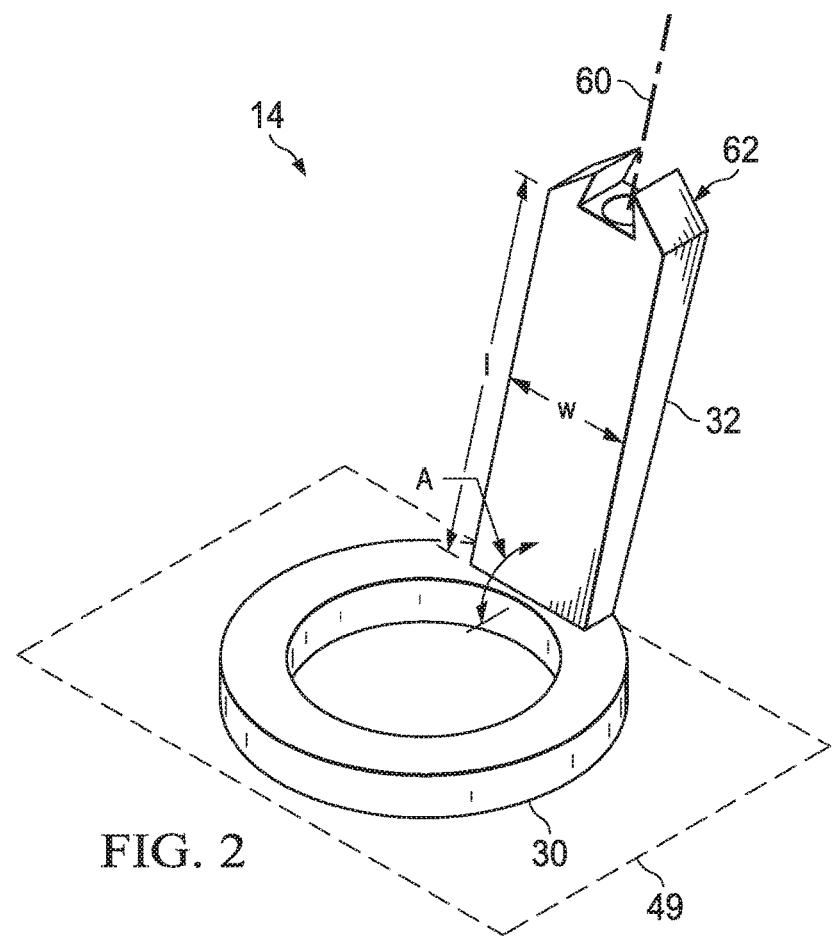
FIG. 2
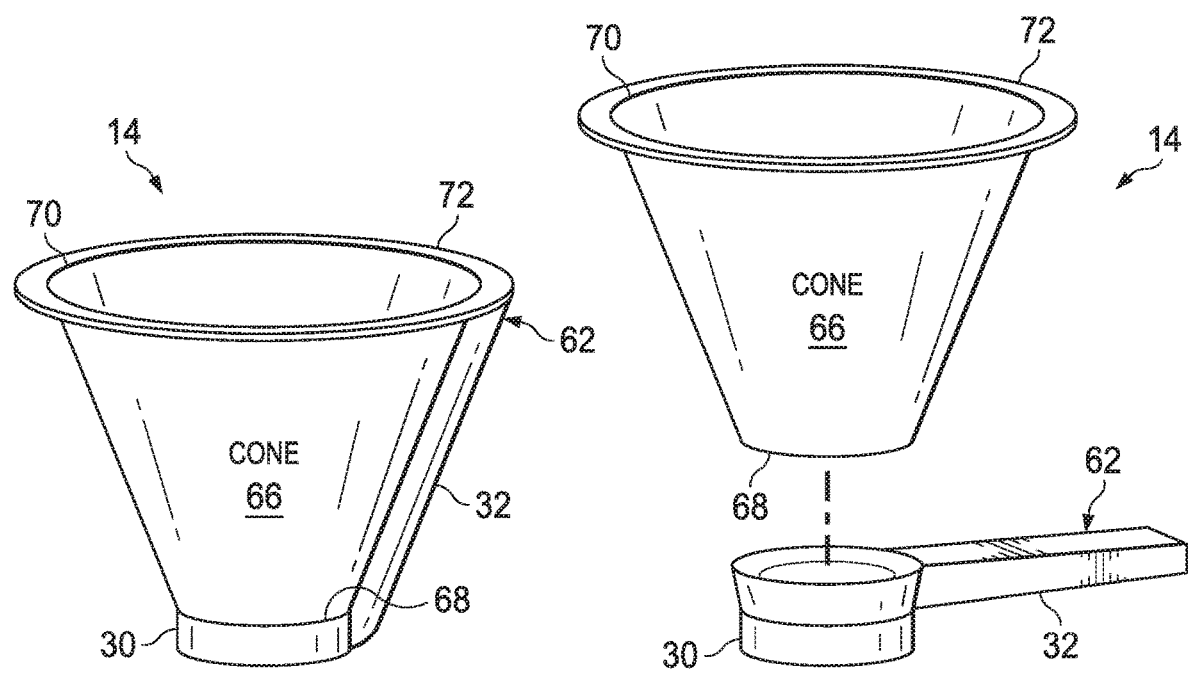
FIG. 3
FIG. 4

PATIENT INTERFACE FOR OPHTHALMIC SURGERY

TECHNICAL FIELD

The present disclosure relates generally to ophthalmic surgery apparatuses, and more specifically to patient interfaces for ophthalmic surgery.

BACKGROUND

In certain kinds of ophthalmic surgery, a laser generates a pulsed laser beam to perform a surgical procedure, e.g., make intrastromal cuts in the cornea or ablate tissue from the cornea. In certain cases, the laser beam creates a photodisruption in the cornea, which can separate tissue, e.g., for removal. The focus of the beam in the cornea has to be precisely determined, e.g., within less than 5 micrometers (μm) in the x, y, and z directions. A patient interface is usually used to hold the eye in position during the procedure. The patient interface is typically affixed to the eye by suction to secure the eye in place.

BRIEF SUMMARY

In certain embodiments, a patient interface apparatus for ophthalmic surgery comprises an annular member and an evacuation conduit. The annular member has an outer side, an inner side, a distal side, and a proximal side. The inner side defines an opening that allows for a laser beam to reach a treatment region of an eye free from reflection or refraction. The proximal side has a contact surface shaped to affix to a surface of the eye, and a groove that defines a suction chamber with the surface of the eye. The evacuation conduit is capable of fluid communication with the suction chamber, and conducts fluid away from the suction chamber to affix the contact surface to the surface of the eye.

Certain embodiments may include one or more of the following features. The patient interface apparatus may include a deformable seal disposed outwardly from the outer circular side. The evacuation conduit may include a conduit coupler that attaches to a suction device. The evacuation conduit may include a conduit coupler that attaches to a laser device. The evacuation conduit may be fixed to the annular member. The patient interface apparatus may include a cone disposed outwardly from the distal side of the annular member. The cone may have a cone coupler that attaches to a laser system. The cone may include the evacuation conduit. The distal side of the annular member may be shaped to receive the cone to removably couple the cone to the annular member.

In certain embodiments, a system for ophthalmic surgery comprises a measurement device and a laser system. The measurement device measures an undeformed treatment region of an eye, where the eye is coupled to a patient interface that leaves the treatment region undeformed. The laser system registers a cutting pattern in the treatment region in accordance with the measurement of the treatment region; directs a laser beam through the patient interface towards the treatment region; and controls a focus of the laser beam to create the cutting pattern in the treatment region.

Certain embodiments may include one or more of the following features. The laser system may register the cutting pattern by: identifying an undeformed feature of the treatment region from the measurement of the treatment region; and registering the cutting pattern relative to the undeformed feature. The measurement device may track movement of the eye, and the laser system further may adjust creation of the remaining cutting pattern in accordance with the movement of the eye. The undeformed feature may be a corneal surface feature or a corneal thickness feature.

BRIEF DESCRIPTION OF THE DRAWINGS

Embodiments of the present disclosure are described by way of example in greater detail with reference to the attached figures, in which:

FIG. 2 illustrates an embodiment of a patient interface where an evacuation conduit is fixed to an annular member;

FIG. 3 illustrates an embodiment of a patient interface where a cone is attached to an annular member and an evacuation conduit;

FIG. 4 illustrates an embodiment of a patient interface where a cone is removably coupled to an annular member and an evacuation conduit.

DESCRIPTION OF EXAMPLE EMBODIMENTS

Referring now to the description and drawings, example embodiments of the disclosed apparatuses, systems, and methods are shown in detail. As apparent to a person of ordinary skill in the field, the disclosed embodiments are exemplary and not exhaustive of all possible embodiments.

Figure 1A:
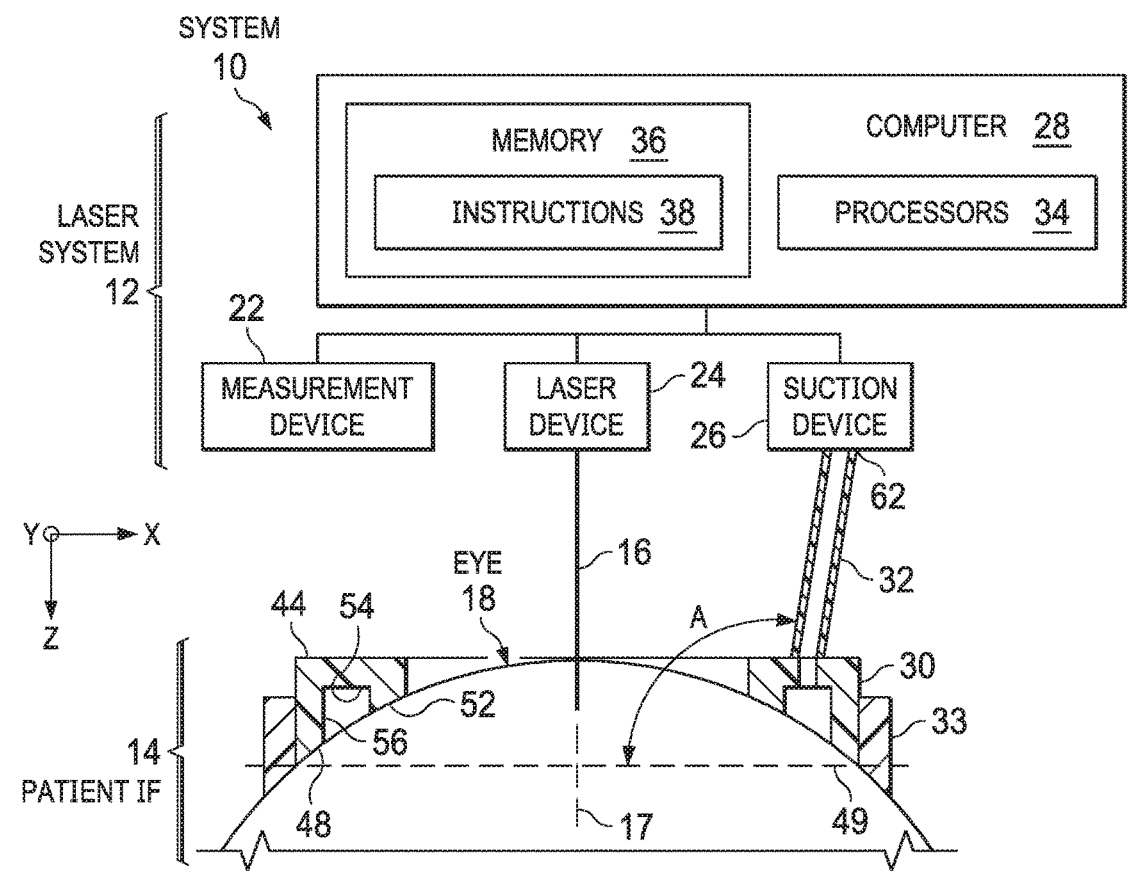
FIGS. 1A and 1B illustrate an embodiment of a system that includes a laser system and a patient interface coupled as shown.
Figure 1B:
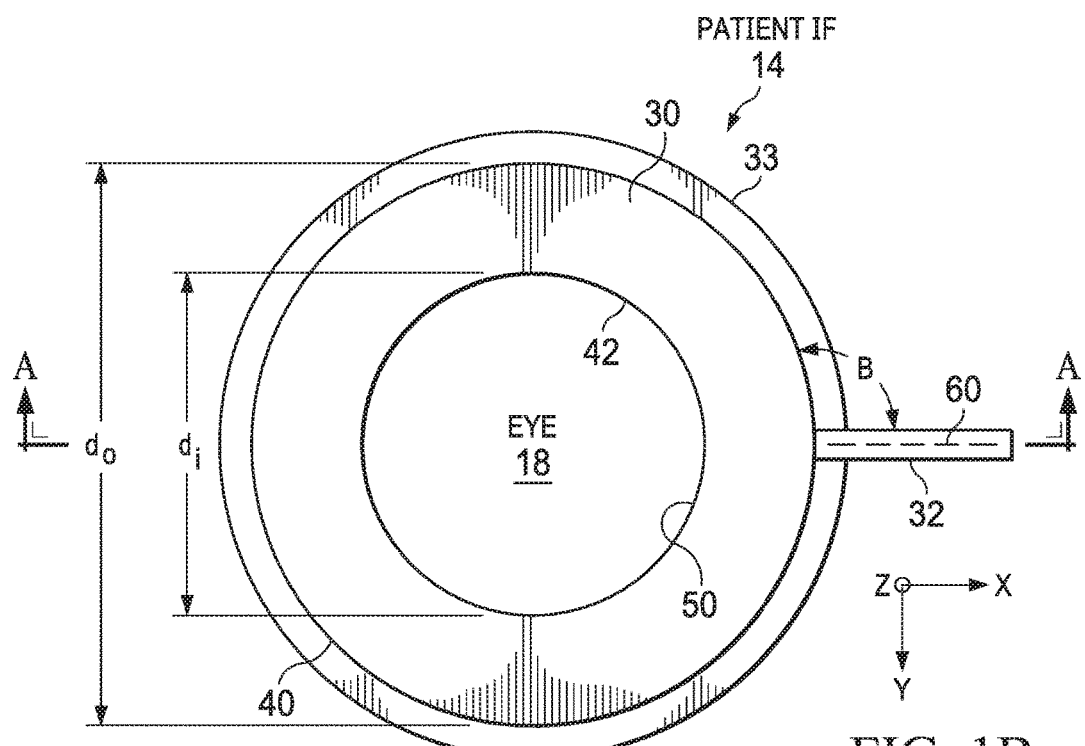

FIGS. 1A and 1B illustrate an embodiment of a system 10 that includes a laser system 12 and a patient interface 14 coupled as shown. FIG. 1B shows a top view of patient interface 14 with a line A-A that bisects interface 14, and FIG. 1A shows a cut away view of patient interface 14 along line A-A. In the embodiment, laser system 12 emits a laser beam 16 to perform a procedure on a treatment region of an eye 18 of a human patient, and patient interface 14 secures eye 18 in place while the procedure is being performed. Patient interface 14 does not deform the treatment region of eye 18 and allows for laser beam 16 to reach the treatment region without reflection or refraction. Since the treatment region of eye 18 is undeformed, laser system 12 can center a treatment plan on a natural feature of the undeformed eye (or "undeformed feature"), such as the apex.

Laser system 12 may perform any suitable ophthalmic procedure on eye 18 that cuts or shapes tissue of eye 18. Examples of such procedures include ophthalmic treatment procedures, e.g., laser assisted in situ Keratomileusis (LASIK) (including flap creation), refractive lenticule extraction (ReLEx), Small Incision Lenticule Extraction (SMILE), photorefractive keratectomy (PRK), laser assisted sub-epithelium keratomileusis (LASEK), intrastromal implant insertion, and keratoplasty.

Laser system 12 includes a measurement device 22, a laser device 24, a suction device 26, and a computer 28 coupled as shown. Measurement device 22 measures a treatment region of eye 18, which is generally the region where laser beam 16 is applied during the surgical procedure. In certain embodiments, the treatment region is the cornea, and measurement device 22 measures the surface topography and/or the thickness of the cornea. In certain embodiments, measurement device 22 may comprise an eye-tracker that measures the position and movement of an eye using, e.g., the surface topography and/or thickness of the cornea. Examples of measurement devices 22 include corneal topography, OCT, Scheimpflug, and projected pattern sequences (e.g., stripes) devices. When the treatment region of eye 18 is undeformed, the cornea has its natural topography and thickness, allowing measurement device 22 to measure the natural (i.e., undeformed) features of eye 18. Examples of such undeformed features include topographical features of the undeformed eye 18, e.g., the apex of the undeformed eye 18. Other examples of such undeformed features include the corneal thickness of the undeformed eye 18, e.g., where the cornea of the undeformed eye 18 has a particular thickness, such as thinnest or thickest.

Laser device 24 generates laser beam 16, which may define an xyz-coordinate system. The axis 17 of laser beam 16 defines the z-axis, which is normal to the xy-plane. Examples of laser 24 include a femtosecond laser, an ultrashort pulse laser that can emit light in the infrared or ultraviolet wavelength range. A femtosecond laser generates a laser beam that can create laser-induced optical breakdowns (LIOBs) in tissue in order to, e.g., create an intrastromal cut in corneal tissue. Laser device 24 may include other components that control beam 40, e.g., a scanner, optical elements, and a focusing objective.

Suction device 26 draws air away from a chamber 56 (described below) of patient interface 14 to lower the air pressure within chamber 56 to create suction that affixes patient interface 14 to eye 18. The air pressure may be lowered to any suitable value, e.g., a value in the range of 300 to 500, 500 to 800, 800 to 1000 millibar (mbar), such as a value in one of the following ranges 500 to 600, 600 to 700, or 700 to 800 mbar. For example, in certain cases, the setpoint could be approximately 650 mbar, but any suitable setpoint may be used (e.g., a setpoint in one of the preceding ranges). Examples of suction device 26 include air pumps.

Computer 28 controls the operation of laser system 12, and includes processors 34 and a memory 36. Processors 34 carry out operations according to instructions 38, which are stored in memory 36. Computer 28 can perform any suitable operations. For example, computer 28 may receive measurements of the treatment region from measurement device 22 and register an intrastromal cutting pattern (e.g., align the pattern with a real-time image of eye 18) in accordance with the measurements. An intrastromal cutting pattern (or "cutting pattern") instructs laser beam 16 where to make intrastromal cuts in eye 18. In some cases, the pattern is calculated to yield a desired refractive correction in eye 18. Examples of procedures using such patterns include Small Incision Lenticule Extraction (SMILE), ReLEx® (Refractive LEnticule Extraction), and radial keratotomy. In other cases, the pattern is designed to yield a cut for a particular purpose. Examples of cuts resulting from such patterns include a flap for a LASIK procedure, a pocket for a corneal implant, a donor corneal transplant extraction, or a region to receive a corneal transplant. The cutting pattern may be registered by identifying an undeformed feature from the measurements, and registering the cutting pattern relative to the undeformed feature. For example, the cutting pattern may be centered directly on the feature. As another example, the cutting pattern may be centered a predetermined distance away from the feature in any suitable direction, such as in the direction of the pupil center. After registering the pattern, computer 28 then instructs laser device 24 to direct laser beam 16 through patient interface 14 towards the treatment region, and controls the focus of laser beam 16 to create the cutting pattern.

Patient interface 14 includes an annular member 30, an evacuation conduit 32, and a seal 33 coupled as shown. Annular member 30 has an annular shape designed to make contact with the anterior surface of eye 18, and evacuation conduit 32 is a conduit designed to allow suction device 26 to draw air away from a chamber 56 of annular member 30 to affix annular member 30 to the anterior surface. Seal 33 prevents air from leaking in between annular member 30 and eye 18 in order to more securely affix annular member 30 to eye 18.

Annular member 30 has an outer side 40, an inner side 42, a distal side 44, and a proximal side 48. Outer side 40 is the outer circular side of annular member 30, and may have any suitable diameter $d_o$, e.g., a value in the range of 10 to 15, 15 to 21, or 21 to 30 millimeters (mm), such as a value in the range 15 to 18, 18 to 20 (e.g., approximately 19 mm), or 20 to 21 mm. Inner side 42 is the inner circular side of annular member 30, and may have any suitable diameter $d_i$, e.g., a value in the range of 5 to 9, 9 to 15, or 15 to 20 mm, such as a value in the range 9 to 10, 10 to 12 (e.g., approximately 11 mm), or 12 to 15 mm. Distal side 44 is the side of annular member 30 that is placed away from eye 18, and proximal side 48 is the side of annular member 30 that is placed towards and in contact with eye 18. Annular member 30 generally defines a plane 49, e.g., the circle formed by the points where outer side 40 meets proximal side 48 generally defines plane 49.

In the illustrated embodiment, inner side 42 defines an opening 50 that allows for laser beam 16 to reach the treatment region. Opening 50 allows laser beam 16 to travel from laser system 12 to the surface of the treatment region free from reflection or refraction. That is, nothing in patient interface 14 reflects, refracts, or otherwise interferes with beam 16. Moreover, opening 50 does not deform, or change the natural shape of, the treatment region of eye 18, allowing for the natural topography and/or corneal thickness of eye 18 to be measured.

Proximal side 48 has a contact surface 52 and a groove 54. Contact surface 52 is shaped to affix to a surface of eye 18. That is, the shape of contact surface 52 is curved to match the shape of the anterior portion of eye 18 that it touches. Groove 54 defines a suction chamber 56 with the surface of eye 18 when contact surface 52 is in contact with the surface. Groove 54 generally follows a circular path defined by annular member 30 and has a cross section of any suitable size and shape. For example, the cross section may be 0.1 to 0.5, 0.5 to 4, or 4 to 8 mm (such as with a value in the range 0.5 to 1, 1 to 3, or 3 to 4 mm) in the z-direction and 0.1 to 0.5, 0.5 to 2, or 2 to 5 mm (such as with a value in the range 0.5 to 0.8, 0.8 to 1.2, or 1.2 to 2 mm) in a direction parallel to a radius of the circular path defined by annular member 30.

Contact surface 52 and groove 54, along with the suction provided by suction device 26, allow for patient interface 14 to affix to eye 18 for the procedure. Other patient interfaces have an additional barrier (e.g., a contact plate) between laser system 12 and the treatment region. However, the additional barrier reflects and/or refracts beam 16, and in some cases deforms eye 18.

Evacuation conduit 32 is in fluid communication with suction chamber 56 and is configured to conduct fluid (which may be a gas or liquid) away from suction chamber 56 to affix the contact surface to the surface of the eye. Evacuation conduit 32 may be shaped like a tube, where the longitudinal axis of the tube defines an axis 60 of evacuation conduit 32. Axis 60 may have any suitable angle A relative to plane 49, e.g., a value in the range of 45 to 90, 90 to 180, or 180 to 200 degrees (such as a value in the range of 90 to 120, 120 to 160, 160 to 170, or 170 to 180 degrees). Axis 60 may have any suitable angle B relative to a tangent of outer side 40 where conduit 32 connects to annular member 30, e.g., a value in the range of 0 to 180 or 180 to 270 degrees (such as a value in the range of 0 to 40, 40 to 80, 80 to 100, 100 to 140, or 140 to 180 degrees). In certain embodiments, evacuation conduit 32 may have a conduit coupler 62 that is shaped to attach to a component of laser system 12. For example, conduit coupler 62 may be shaped to attach to suction device 26 or to laser device 24.

Seal 33 is disposed outwardly from outer side 40 and forms a seal to prevent air from leaking in between annular member 30 and eye 18 in order to more securely affix annular member 30 to eye 18. Seal 33 may comprise any suitable deformable material, e.g., a deformable, biocompatible, sterilizable material.

FIGS. 2-4 illustrate embodiments of patient interface 14. FIG. 2 illustrates an embodiment of patient interface 14 where evacuation conduit 32 is fixed to annular member 30. Evacuation conduit 32 may have any suitable dimensions. For example, length 1 and width w may be selected to form a convenient handle that allows a user to grasp interface 14, such as a length 1 within a range of 5 to 10, 10 to 50, or 50 to 100 mm and a width w within a range of 2 to 5, 5 to 10, or 10 to 20 mm. Axis 60 may have any suitable angle A relative to plane 49, e.g., an angle that yields the convenient handle. Conduit coupler 62 may attach to laser system 12 in any suitable manner. For example, coupler 62 may have a shape that interlocks with a component (e.g., suction device 26 or to laser device 24) of laser system 12.

FIGS. 3 and 4 illustrate embodiments of patient interface 14 with a cone 66. Cone 66 has a proximate side 68, a distal side 70, and a cone coupler 72. Proximate side 68 is placed closer to eye 18 and distal side 70 is placed away from eye 18. Proximate side 68 is designed to be disposed outwardly from the distal side of annular member 30 and may have a diameter that is approximately the same as that of annular member 30. Distal side 70 may have any suitable diameter that may be larger than or equal to that of proximate side 68. For example, the diameter of distal side 70 may be sized to allow cone 66 to be conveniently used in system 12, e.g., sized to allow cone 66 to be coupled to system 12. Cone coupler 72 may be located at distal side 70 and may be shaped to attach to laser device 24. For example, cone coupler 72 may be shaped to interlock with a component through which laser device 24 emits beam 16.

FIG. 3 illustrates an embodiment of patient interface 14 where cone 66 is attached to annular member 30 and evacuation conduit 32. In the embodiment, proximate side 68 of cone 66 is attached to the distal side of annular member 30. Evacuation conduit 32 may be attached to cone 66 or may be formed within the side of cone 66.

FIG. 4 illustrates an embodiment of patient interface 14 where cone 66 is removably coupled to annular member 30 and evacuation conduit 32. In the embodiment, the distal side of annular member 30 is shaped to receive proximate side 68 of cone 66.

Figure 5:
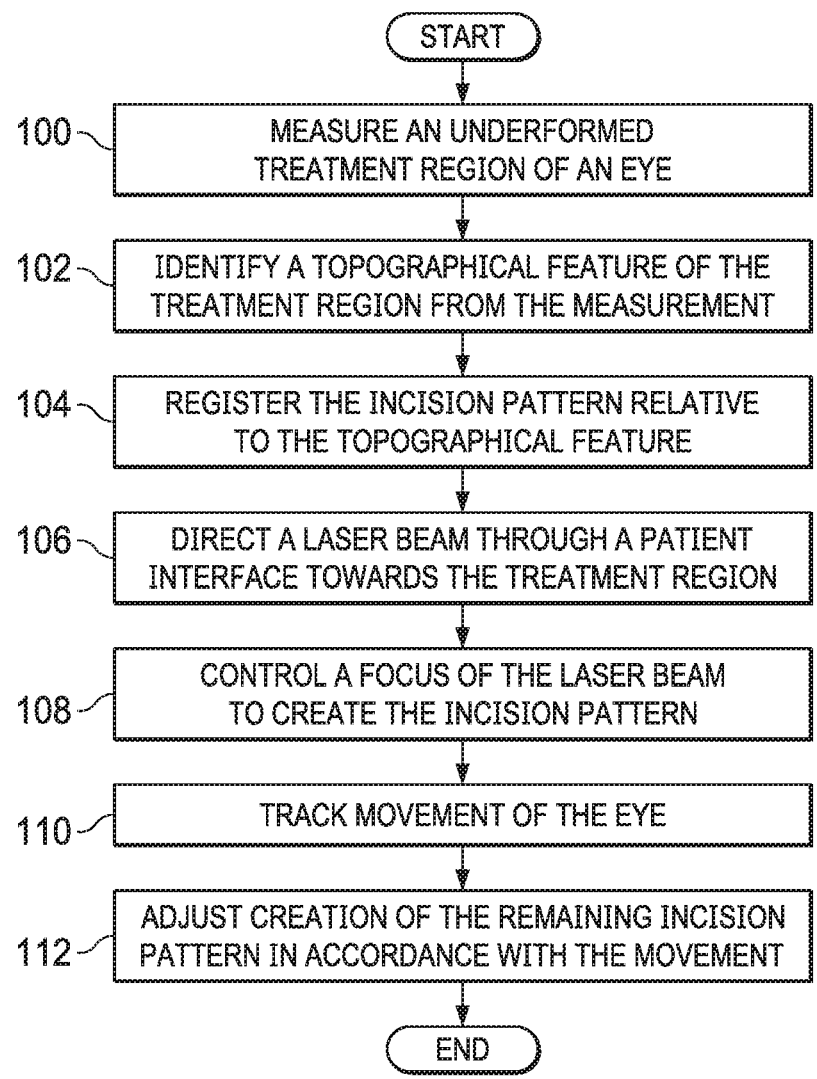
FIG. 5 illustrates an example of a method for creating intrastromal cuts that may be performed by the system of FIG. 1.

FIG. 5 illustrates an example of a method for creating intrastromal cuts that may be performed by the system of FIG. 1. In the example, patient interface 14 that does not deform eye 18, so laser system 12 can register the cutting pattern using an undeformed feature of eye 18. The method starts at step 100, where measurement device 22 measures a treatment region of eye 18. Eye 18 is coupled to patient interface 14 that leaves the treatment region undeformed.

Computer 28 of laser system 12 registers a cutting pattern in the treatment region in accordance with the measurement at steps 102 and 104. Computer 28 identifies an undeformed feature of the treatment region from the measurement at step 102, and registers the cutting pattern relative to the undeformed feature at step 104. For example, computer 28 identifies the apex of eye 18 and centers the cutting pattern at or near the apex. As another example, computer 28 identifies the location where the cornea of eye 18 is the thinnest and centers the cutting pattern at or near the location. At step 106, laser device 24 directs laser beam 16 through patient interface 14 towards the treatment region and controls the focus of laser beam 16 to create the cutting pattern in the treatment region.

Measurement device 22 tracks movement of eye 18 at step 110. For example, measurement device 22 determines the apex has translated in a distance d in a particular direction in the xy plane. Computer 28 adjusts creation of the remaining cutting pattern in accordance with the movement of the eye. For example, computer 28 realigns the cutting pattern to according to the translation of the apex. The method then ends.

A component of the systems and apparatuses disclosed herein may include an interface, logic, memory, and/or other suitable element, any of which may include hardware and/or software. An interface can receive input, provide output, process the input and/or output, and/or perform other suitable operations. Logic can perform the operations of a component, for example, execute instructions to generate output from input. Logic may be encoded in memory and may perform operations when executed by a computer. Logic may be a processor, such as one or more computers, one or more microprocessors, one or more applications, and/or other logic. A memory can store information and may comprise one or more tangible, computer-readable, and/or computer-executable storage media. Examples of memory include computer memory (e.g., Random Access Memory (RAM) or Read Only Memory (ROM)), mass storage media (e.g., a hard disk), removable storage media (e.g., a Compact Disk (CD) or a Digital Video Disk (DVD)), database and/or network storage (e.g., a server), and/or other computer-readable media. In particular embodiments, operations of the embodiments may be performed by one or more computer readable media storing and/or encoded with a computer program, software, and/or other computer-executable instructions.

Although this disclosure has been described in terms of certain embodiments, modifications (such as substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, and the operations of the systems and apparatuses may be performed by more, fewer, or other components. As another example, modifications may be made to the methods disclosed herein. The methods may include more, fewer, or other steps, and the steps may be performed in any suitable order.

What is claimed is:

1. A patient interface apparatus for ophthalmic surgery, comprising:
   an annular member having an outer side, an inner side opposite the outer side, a distal side, and a proximal side opposite the distal side:
   the inner side defining an opening that allows for a laser beam to reach a treatment region of an eye free from reflection or refraction; and
   the proximal side having:

a contact surface shaped to affix to a surface of the eye; and a groove that defines a suction chamber with the surface of the eye;

an evacuation conduit capable of fluid communication with the suction chamber, the evacuation conduit configured to conduct fluid away from the suction chamber to affix the contact surface to the surface of the eye; wherein the evacuation conduit is coupled to the distal side of the annular member and extends from the distal side of the annular member; wherein the evacuation conduit forms a rigid handle that allows a user to grasp the patient interface; and a cone disposed outwardly from the distal side of the annular member, the cone having inner and outer surfaces, the outer surface of the cone contacting a surface of the rigid handle along an entire length of the rigid handle.

2. The patient interface apparatus of claim 1, further comprising a deformable seal disposed outwardly from the outer side.

3. The patient interface apparatus of claim 1, wherein the evacuation conduit comprises a conduit coupler configured to attach to a suction device.

4. The patient interface apparatus of claim 1, wherein the evacuation conduit comprises a conduit coupler configured to attach to a laser device.

5. The patient interface apparatus of claim 1, wherein the evacuation conduit is fixed to the annular member.

6. The patient interface apparatus of claim 1, the cone having a cone coupler configured to attach to a laser system.

7. The patient interface apparatus of claim 1, wherein the cone comprises the evacuation conduit.

8. The patient interface apparatus of claim 1, wherein the distal side of the annular member is shaped to receive the cone to removably couple the cone to the annular member.

9. The patient interface apparatus of claim 1 wherein a longitudinal axis of the evacuation conduit is disposed at an angle of between 90 degrees and 120 degrees with respect to the distal side of the annular member.

10. The patient interface apparatus of claim 1 further comprising a seal disposed outwardly from the outer side of the annular member.

11. The patient interface apparatus of claim 1 wherein the rigid handle has a width between 2 and 20 mm and a length between 5 and 100 mm.

* * * * *